(12) United States Patent
Vandenberghe (10) Patent No.: US 7,897,926 B2
(45) Date of Patent: Mar. 1, 2011

(54) THREE-DIMENSIONAL TIME-OF-FLIGHT PET WITH COARSE ANGULAR AND SLICE REBINNING

(75) Inventor: Stefaan J. C. Vandenberghe, Philadelphia, PA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 674 days.

(21) Appl. No.: 11/911,240

(22) PCT Filed: Mar. 28, 2006

(86) PCT No.: PCT/IB2006/050942
§ 371 (c)(1),
(2), (4) Date: Oct. 11, 2007

(87) PCT Pub. No.: WO2006/109203
PCT Pub. Date: Oct. 19, 2006

(65) Prior Publication Data
US 2009/0124900 A1    May 14, 2009

Related U.S. Application Data

(60) Provisional application No. 60/671,158, filed on Apr. 14, 2005.

(51) Int. Cl.
*G01T 1/166* (2006.01)
*G01T 1/29* (2006.01)

(52) U.S. Cl. .................... 250/363.04; 250/363.03; 382/131; 378/21

(58) Field of Classification Search ............ 250/360.03, 250/363.04, 366; 378/901, 21; 382/131; 132/131
See application file for complete search history.

(56) References Cited

U.S. PATENT DOCUMENTS

| 4,559,597 | A  | * | 12/1985 | Mullani | 600/407 |
| 5,742,056 | A  |   | 4/1998  | Valentino et al. | |
| 5,744,802 | A  |   | 4/1998  | Muehllehner et al. | |
| 6,327,326 | B1 | * | 12/2001 | Flohr et al. | 378/8 |
| 6,462,342 | B1 |   | 10/2002 | Stearns | |
| 6,804,325 | B1 |   | 10/2004 | Smith | |
| 7,417,231 | B2 | * | 8/2008  | Defrise et al. | 250/363.04 |
| 2003/0161521 | A1 | * | 8/2003 | Newport et al. | 382/131 |

(Continued)

OTHER PUBLICATIONS

Daube-Witherspoon, M. E., et al.; Treatment of Axial Data in Three-Dimensional PET; 1987; Journal of Nuclear Medicine; 28(11)1717-1724.

(Continued)

*Primary Examiner*—David P Porta
*Assistant Examiner*—Yara B Green (57) ABSTRACT

In a time-of-flight positron emission tomography (TOF-PET) imaging method, three-dimensional time-of-flight line-of-response (TOF-LOR) data are acquired. Each TOF-LOR corresponds to a line-of-response with time-of-flight spatial localization. The TOF-LOR data are slice-binned into a plurality of two-dimensional TOF-LOR data sets based on the time-of-flight spatial localization. At least some of the slice-binned TOF-LOR data correspond to lines of response that are oblique to the two-dimensional data sets. The TOF-LOR data are coarsely angularly rebinned to a plurality of coarse angular bins each having an angular span of at least about 10°. The coarsely angularly binned TOF-LOR data are reconstructed to produce the image slice.

16 Claims, 4 Drawing Sheets

U.S. PATENT DOCUMENTS

2005/0047679 A1* 3/2005 Riddell et al. ............... 382/298
2006/0102846 A1* 5/2006 Manjeshwar et al. ... 250/363.03

OTHER PUBLICATIONS

Defrise, M., et al.; Exact and Approximate Rebinning Algorithms for 3-D PET Data; 1997; IEEE Trans. on Medical Imaging; 16(2)145-158.

Lewitt, R., et al.; Three-dimensional image reconstruction for PET by multi-slice rebinning and axial image filtering; 1994; Phys. Med. Biol.; 39:321-339.

Moses, W. W.; Time of Flight in PET Revisited; 2003; IEEE Trans. on Nuclear Science; 50(5)1325-1330.

Moses, W. W., et al.; Prospects for Time-of-Flight PET using LSO Scintillator; 1999; IEEE Trans. on Nuclear Science; NS46; pp. 474-478.

Mullani, N., et al.; Sensitivity Improvement of TOF-PET by the Utilization of the Inter-Slice Coincidences; 1982; IEEE Trans. on Nuclear Science; NS-29; pp. 479-483.

Politte, D. G., et al.; Image-Reconstruction of Data from Super PETT I: A First-Generation Time-of-Flight Positron-Emission Tomograph; 1986; IEEE Trans. on Nuclear Science; NS-33(1)428-434.

Snyder, D. L., et al.; A mathematical model for positron-emission tomography systems having Time-of-Flight measurements; 1981; IEEE Trans. on Nuclear Science; NS-28(3)3575-3583.

Surti, S., et al.; Investigation of Lanthanum Scintillators for 3-D PET; 2003; IEEE Trans. on Nuclear Science; 50(3) 348-354.

Tomitani, T.; Image Reconstruction and Noise Evaluation in Photon Time-of-Flight Assisted Positron Emission Tomography; 1981; IEEE Trans. on Nuclear Science, NS-28(6)4582-4589.

Vandenberghe, S., et al.; Fast reconstruction of 3D time-of flight PET data by axial rebinning and transverse mashing; 2006; Phys. Med. Biol.; 51:1603-1621.

Yamamoto, M., et al.; Time-of-Flight positron imaging and the resolution improvement by an iterative method; 1989; IEEE Trans. on Nuclear Science; 36(1)998-1002.

* cited by examiner

THREE-DIMENSIONAL TIME-OF-FLIGHT PET WITH COARSE ANGULAR AND SLICE REBINNING

CROSS REFERENCE TO RELATED APPLICATIONS

This application claims the benefit of U.S. provisional application Ser. No. 60/671,158 filed Apr. 14, 2005, which is incorporated herein by reference.

The following relates to the radiation detection arts. It particularly relates to time-of-flight positron emission tomography (TOF-PET) imaging, and will be described with particular reference thereto. However, the following relates more generally to imaging, spectroscopy, and the like using radioactive tracers or imaging agents that produce simultaneous radiation particle emission events.

In PET, a radiopharmaceutical is administered to a human patient or other imaging subject. The radiopharmaceutical produces radiation decay events that emit positrons, which travel a very short distance before rapidly interacting with an electron of the surrounding imaging subject in an electron-positron annihilation event to produce two oppositely directed gamma rays. The gamma rays are detected by radiation detectors surrounding the imaging subject as two substantially simultaneous radiation detection events that define a line of reaction (LOR) therebetween.

Although the gamma rays are detected "substantially simultaneously", if one of the two involved radiation detectors is closer to the electron-positron annihilation event than the other radiation detector, then there will be a small time difference between the two radiation detection events. Since gamma rays travel at the speed of light, this time difference between detections is typically around a few nanoseconds or less. In TOF-PET, the radiation detectors operate at a sufficiently high speed to enable measurement of this small time-of-flight difference, which is then used to localize the electron-positron annihilation event to a segment of the LOR. The acquired LOR data define projection data that can be reconstructed by filtered backprojection, iterative backprojection, or other algorithms to produce a reconstructed image.

One factor in the reconstruction speed and accuracy is the angular binning resolution. A typical PET scanner has one or more rings of detectors, with each detector ring including 600-700 detector pixels. Thus, the angular resolution (acquired angular bin size) of the acquired LOR data within the transverse plane of the detector ring is around 0.5°-1°. By rebinning the LOR data to fewer angular bins each spanning a larger angular bin size or interval, reconstruction speed is increased. However, angular rebinning can generally be expected to degrade image resolution to an extent approximately commensurate with the reduced angular resolution of the angularly rebinned LOR data.

In three-dimensional PET, multiple rings of radiation detectors surround the imaging subject to provide imaging data for a plurality of slices. The oppositely directed gamma rays in general may be detected by radiation detectors on the same or different rings. Gamma ray pairs detected by radiation detectors of the same ring emanated from a positron-electron annihilation event located in a plane containing that ring; however, gamma ray pairs detected by radiation detectors of different rings emanated from a positron-electron annihilation event located in a volume bounded by the rings that detected the gamma rays. In one reconstruction approach, only LOR data corresponding to coincident gamma rays detected by the same ring are processed. This approach allows each slice to be separately reconstructed, but results in the discarding of a large amount of LOR data. To utilize all the LOR data including LOR projections acquired using two different detector rings, the backprojection or other reconstruction is performed three-dimensionally, which is computationally intensive and requires large amounts of data storage.

The following contemplates improved apparatuses and methods that overcome the aforementioned limitations and others.

According to one aspect, an imaging method is provided. Three-dimensional positron emission tomography time-of-flight line-of-response (TOF-LOR) data are acquired. Each TOF-LOR corresponds to a line-of-response with time-of-flight spatial localization. The TOF-LOR data are slice-binned into a plurality of two-dimensional TOF-LOR data sets based on the time-of-flight spatial localization. At least some of the slice-binned TOF-LOR data correspond to lines of response that are oblique to the two-dimensional data sets. The two-dimensional TOF-LOR data sets are reconstructed into corresponding image slices defining a three-dimensional reconstructed image.

According to another aspect, a positron emission tomography (PET) scanner is disclosed for performing the imaging method set forth in the first paragraph of this Summary.

According to another aspect, a processor is disclosed that is programmed to perform the imaging method set forth in the first paragraph of this Summary.

According to another aspect, a time of flight positron emission tomography scanner is disclosed. A means is provided for acquiring three-dimensional positron emission tomography time-of-flight line-of-response (TOF-LOR) data. Each TOF-LOR corresponds to a line-of-response with time-of-flight spatial localization. A means is provided for slice-binning the TOF-LOR data into a plurality of two-dimensional TOF-LOR data sets based on the time-of-flight spatial localization. At least some of the slice-binned TOF-LOR data correspond to lines of response that are oblique to the two-dimensional data sets. A means is provided for reconstructing the two-dimensional TOF-LOR data sets into corresponding image slices defining a three-dimensional reconstructed image.

According to another aspect, an imaging method is provided. Positron emission tomography time-of-flight line-of-response (TOF-LOR) data are acquired. Each TOF-LOR corresponds to a line-of-response with time-of-flight spatial localization. The TOF-LOR data are coarsely angularly rebinned to a plurality of coarse angular bins each having an angular span of at least about 10°. The coarsely angularly binned TOF-LOR data are reconstructed to produce the image slice.

One advantage resides in providing fast TOF-PET image reconstruction.

Another advantage resides in providing high resolution TOF-PET image reconstruction.

Another advantage resides in enabling TOF-PET image reconstruction on a slice-by-slice basis without discarding LOR data acquired by different detector rings.

Another advantage resides in providing fast TOF-PET image reconstruction using coarse angular rebinning without concomitant loss of image resolution.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

Figure 1:
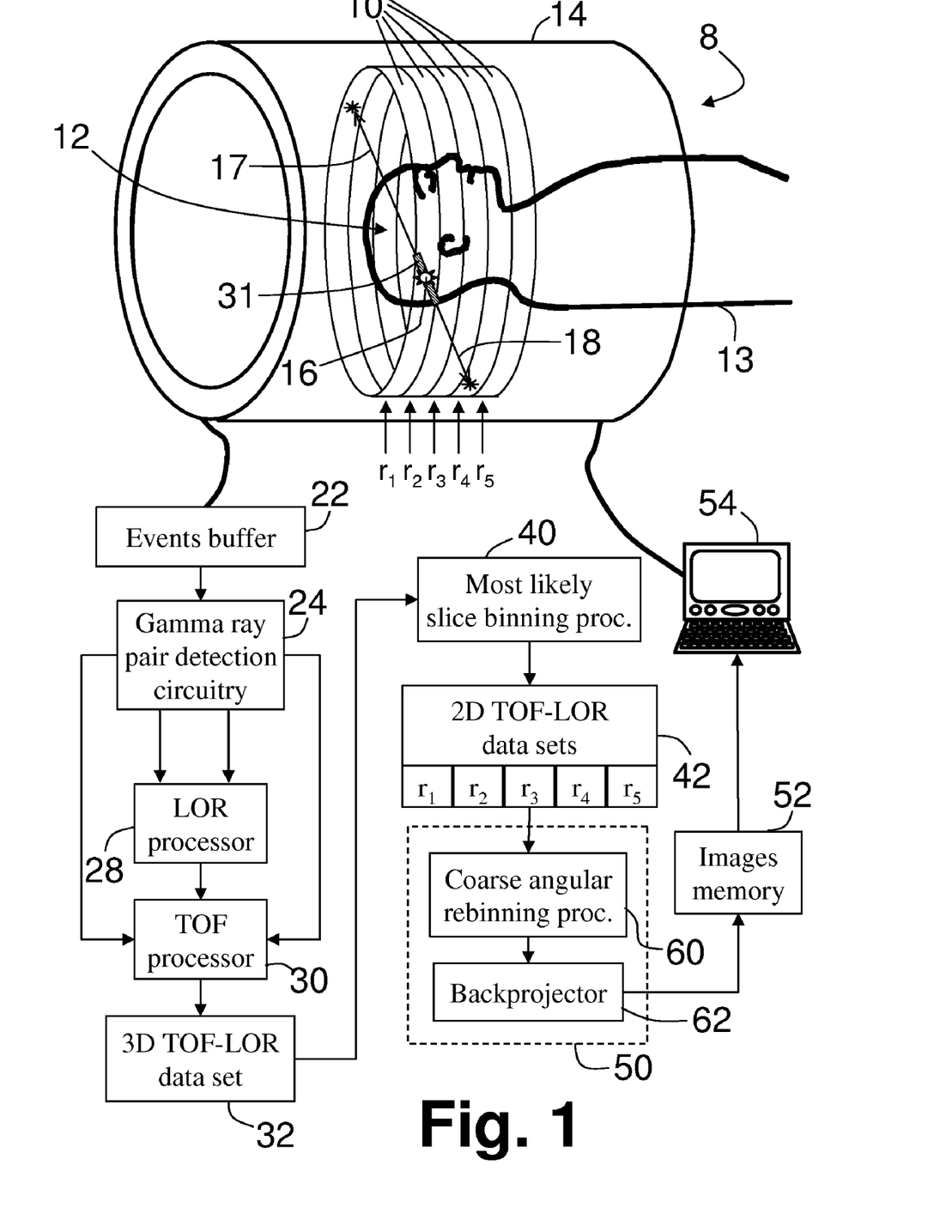
FIG. 1 diagrammatically shows a TOF-PET system employing coarse angular and most likely slice rebinning.

With reference to FIG. 1, a time-of-flight positron emission tomography (TOF-PET) scanner 8 includes a plurality of rings 10 of radiation detectors arranged to view an imaging region 12 inside of which an imaging subject is disposed. In FIG. 1, the imaging subject is the head of a human patient 13; however, other anatomical regions can be imaged, and moreover the imaging subject can be non-human. In FIG. 1, five radiation detector rings 10 are illustrated for ease of explanation, indexed as $r_1$, $r_2$, $r_3$, $r_4$, $r_5$, respectively; however, typically 20-60 or more detector rings are included for high resolution three-dimensional imaging. Moreover, it is to be appreciated that the radiation detector rings 10 are diagrammatically illustrated; typically the radiation detectors are housed within a housing 14 of the scanner 8 and thus are not visible from the outside. Typically, each radiation detector ring 10 includes hundreds of radiation detector, for example defining 600-700 radiation detector pixels per ring.

A suitable radiopharmaceutical is administered to the patient or other imaging subject prior to initiation of TOF-PET imaging. The radiopharmaceutical includes a radioactive substance that undergoes radioactive decay events that emit positrons. The positrons rapidly annihilate with nearby electrons of the imaging subject. One example positron-electron annihilation event 16 is diagrammatically indicated in FIG. 1. Each positron-electron annihilation event produces two oppositely directed gamma rays having energies of 511 keV. The example positron-electron annihilation event produces gamma rays 17, 18. Other radiopharmaceuticals having radioactive decays causing multiple particles to be emitted along opposing or otherwise predictable relative trajectories are also contemplated. The gamma rays travel at the speed of light, i.e. $\sim 3 \times 10^8$ meters/sec. Since the imaging region 12 typically has a diameter or other characteristic dimension of about two meters or less, the time-of-flight for a gamma particle from the position of the positron-electron annihilation event to one of the detectors of the plurality of radiation detectors 10 is about a few nanoseconds or less. Thus, the two oppositely directed gamma rays strike two of the radiation detectors substantially simultaneously.

The two gamma rays may be detected by radiation detectors on the same radiation detector ring. In this case, the corresponding LOR lies in the plane of the radiation detector ring, and it is readily apparent that the positron-electron annihilation event lies within a spatial slice defined by the radiation detector ring.

More generally, however, the two gamma rays may be detected by two different radiation detector rings. The illustrated gamma rays 17, 18, for example, are detected by two different ones of the radiation detector rings 10. Specifically, gamma ray 17 is detected by radiation detector ring $r_1$ while gamma ray 18 is detected by radiation detector ring $r_4$. In this case, the corresponding LOR is not coplanar with any one of the detector rings 10, and the positron-electron annihilation event 16 could be located in any one of the four spatial slices defined by the detector rings $r_1$, $r_2$, $r_3$, $r_4$.

The radiation detectors localize each particle detection, for example using Anger logic or other processing, to determine the particle energy and precise location of the detection. The logic can be integrated into the radiation detector electronics, or can be housed within the PET housing 14, or can be located off the scanner. The resulting radiation detection events are stored in a list of events buffer 22, with each detection event tagged or annotated by the time of detection to facilitate TOF processing. A gamma ray pair detection circuitry 24 processes the radiation detection events to identify pairs of substantially simultaneous gamma ray detections belonging to corresponding electron-positron annihilation events. This processing can include, for example, energy windowing (that is, discarding radiation detection events outside of a selected energy filtering window disposed about 511 keV) and coincidence-detecting circuitry (that is, discarding radiation detection event pairs temporally separated from each other by greater than a selected time filtering interval).

When a gamma ray pair is identified, a line-of-response (LOR) processor 28 processes the spatial information pertaining to the two gamma ray detection events to identify a spatial line of response (LOR) connecting the two gamma ray detections. Since the two gamma rays are emitted along diametrically opposed paths, the electron-positron annihilation event is known to have occurred somewhere on the LOR.

In TOF-PET, the radiation detectors of the detector rings 10 have sufficiently high temporal resolution to detect a time-of-flight difference between the two "substantially simultaneous" gamma ray detections. A time-of-flight processor 30 analyzes the time difference between the times of the two gamma ray detection events to localize the positron-electron annihilation event along the LOR. A time-of-flight line-of-response (TOF-LOR), such as a histoprojection, is determined based on time-of-flight information. In FIG. 1, a histoprojection 31 corresponding to the example positron-electron annihilation event 16 is indicated. Because the example positron-electron annihilation event 16 is closer to the radiation detector that detects the gamma ray 18 as compared with the radiation detector that detects the gamma ray 17, the time-of-flight for gamma ray 18 is shorter than the time-of-flight for the gamma ray 17, and so the TOF-LOR or histoprojection 31 is correspondingly shifted along the LOR toward the radiation detector that detects the gamma ray 18.

The TOF-LOR 31 has a finite length along the LOR that is non-zero due to the finite temporal resolution of the radiation detectors. In some embodiments, each TOF-LOR embodies or represents a Gaussian or other probability distribution indicative of the position of the positron-electron annihilation event along the LOR. In other embodiments, the TOF-LOR embodies or represents a constant value over a statistical width such as a full-width-at-half-maximum (FWHM) of the probability distribution along the LOR. The TOF-LOR data can employ other suitable representations of localization of the positron-electron annihilation event along the LOR based on the TOF information. The resulting TOF-LOR data, accumulated for a large number of positron-electron annihilation events, are stored as a set of three-dimensional TOF-LOR data 32.

Figure 2:
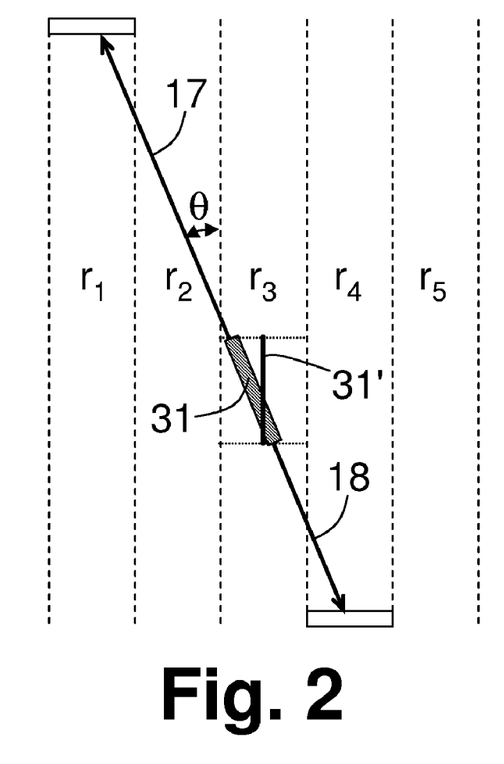
FIG. 2 diagrammatically shows slice-binning for binning a three-dimensional TOF-LOR data set into a plurality of two-dimensional TOF-LOR data sets based on the time-of-flight localization.

With continuing reference to FIG. 1 and with further reference to FIG. 2, a most likely slice binning processor 40 bins the set of three-dimensional TOF-LOR data 32 into a plurality of two-dimensional TOF-LOR data sets 42 based on the time of flight localization of the TOF-LORs. The slice-binning suitably bins the TOF-LOR data 32 into spatial slices defined by the radiation detector rings. For the illustrated embodiment with five detector rings 10, the most likely slice binning processor 40 bins the three-dimensional TOF-LOR data 32 into five two-dimensional TOF-LOR data sets 42 corresponding to the detector rings $r_1$, $r_2$, $r_3$, $r_4$, $r_5$, respectively.

The slice-binning suitably bins each TOF-LOR to that spatial slice containing at least the central portion of the TOF-LOR. If each TOF-LOR represents a Gaussian or other probability distribution indicative of the underlying positron-electron annihilation event then it is straightforward to determine the Gaussian peak or other mean or average value of the probability distribution indicative of a most likely spatial position of the positron-electron annihilation event. The slice binning processor 40 then suitably bins each TOF-LOR to that spatial slice containing the most likely spatial position of the positron-electron annihilation event corresponding to the TOF-LOR.

In FIG. 2, the example TOF-LOR 31 is seen to be suitably binned to the slice defined by the radiation detector ring $r_3$, which contains most or all of the TOF-LOR 31. In some embodiments, the slice-binning includes projecting each TOF-LOR into the slice into which that TOF-LOR is slice-binned. This is shown in FIG. 2, where the example TOF-LOR 31 is projected into the slice defined by the detector ring $r_3$ to define the slice-binned TOF-LOR 31' lying within the slice defined by the detector ring $r_3$. In other contemplated embodiments, the TOF-LOR is suitably rotated into the slice, producing a generally larger TOF-LOR in the two-dimensional data set. Optionally, the TOF-LOR can be binned into two or more slices with its contribution to each slice weighted in accordance with the probability of the event occurring in each slice.

The following is one quantitative example of one suitable approach for slice-binning. In this example, each LOR has a first endpoint $(x_1,y_1,z_1)$ determined by a radiation detection event occurring at a time $t_1$, and a second endpoint $(x_2,y_2,z_2)$ determined by a radiation detection event occurring at a time $t_2$. The time-of-flight information is quantified by a time difference $\Delta t = t_2 - t_1$. A most likely slice ($z_{ML}$) is suitably determined as:

$$z_{ML} = \frac{(z_1 + z_2)}{2} - c\frac{\Delta t}{2}\frac{(z_2 - z_1)}{d}, \quad (1)$$

where "c" denotes the speed of light and d denotes the length of the LOR, given by:

$$d = \sqrt{(x_2-x_1)^2 + (y_2-y_1)^2 + (z_2-z_1)^2} \quad (2).$$

The first term of $z_{ML}$ is the average slice position between the first and second endpoints of the LOR, while the second term of $z_{ML}$ is a correction or adjustment term that accounts for the TOF information.

With continuing reference to FIG. 2, the angle of the LOR respective to the image spatial slice to which it is binned is denoted as θ. Using Gaussian kernel representations for the time-of-flight information, the spatial uncertainty of the time-of-flight ($FWHM_{TOF}$) is computed by multiplying the temporal time-of-flight uncertainty by the speed of light (c=3.0× $10^{11}$ millimeters/sec). An estimate of a likelihood of slice misplacement by the most likely slice binning processor 40 is suitably computed as:

$$FWHM_{slice} = \sin(\theta) \cdot FWHM_{TOF} \quad (3).$$

For a TOF-PET scanner having a most oblique LOR in a system with 15° axial opening angle (θ(max)=7.5°) and $FWHM_{TOF}$=300 picoseconds (90 millimeters):

$$FWHM_{slice} = \sin(7.5°) \cdot (90 \text{ millimeters}) = 12 \text{ millimeters} \quad (4).$$

This is the maximum slice misplacement. For less oblique LORs (that is, θ<7.5°), the error will be smaller. Advantageously, the slice misplacement error is only weakly dependent of the position of the TOF-LOR within the field of view of the PET scanner, and is substantially determined by the time-of-flight resolution.

Each of the two-dimensional TOF-LOR data sets 42 is reconstructed by a two-dimensional reconstruction processor 50 to produce a corresponding image slice. The reconstructed image slices collectively define a three-dimensional reconstructed image which is stored in an images memory 52. The three-dimensional reconstructed image can be displayed on a user interface 54, printed, stored, communicated over an intranet or the Internet, or otherwise used. In the illustrated embodiment, the user interface 54 also enables a radiologist or other user to control the TOF-PET scanner 8; in other embodiments, a separate controller or control computer may be provided.

With continuing reference to FIG. 1, the two-dimensional reconstruction processor 50 includes a coarse angular rebinning processor 60 that rebins the two-dimensional TOF-LOR data set to a plurality of coarse angular bins. In some embodiments, each angular bin has an angular span of at least about 10°. In some embodiments, the number of angular bins is less than about twenty bins collectively spanning an angular span of 180°. A backprojector 62 backprojects the coarsely angularly rebinned TOF-LOR data to produce the reconstructed image slice. In some embodiments, the backprojector 62 is a filtered backprojector that produces the reconstructed image slice in a single iteration. In other embodiments, the backprojector 62 employs iterative backprojecting of the two-dimensional TOF-LOR data to produce the image slice. Other reconstruction algorithms can also be used to reconstruct the coarsely angularly rebinned TOF-LOR data to produce the reconstructed image slice.

Figure 3:
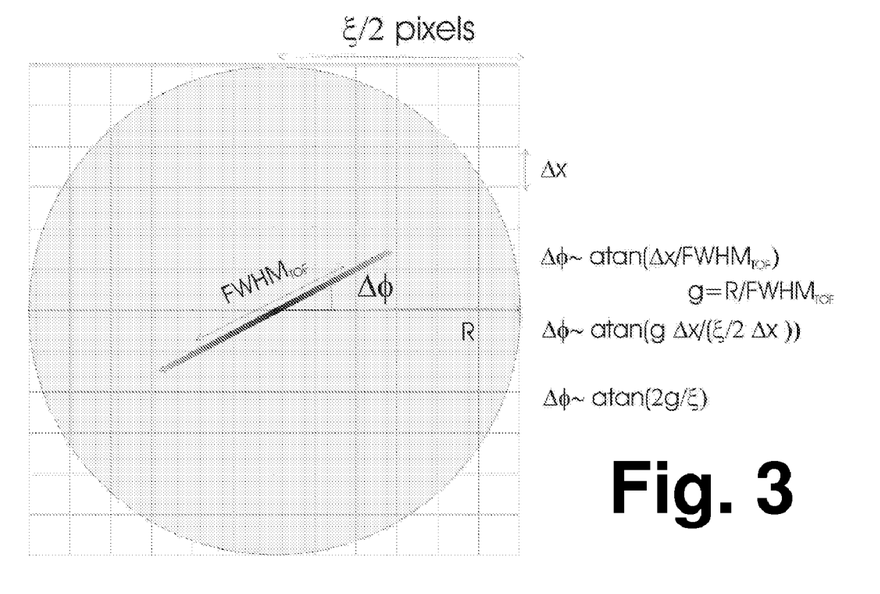
FIG. 3 diagrammatically shows a derivation of a minimum bin size for coarse angular rebinning of two-dimensional TOF-LOR data.

With reference to FIG. 3, the coarse rebinning, for example using bins with angular spans of at least about 10°, does not substantially degrade the resolution of the reconstructed image. For Gaussian time-of-flight kernels, the spatial time-of-flight resolution is suitably denoted $FWHM_{TOF}$. A region of interest of radius R is considered, spanned by ξ pixels (that is, $\Delta x \cdot R = \xi$ where $\Delta x$ is the pixel size as shown in FIG. 3). Defining $g = R/FWHM_{TOF}$ where R is a radius of a region of interest, resolution is not degraded if the error due to angular rebinning is less than the pixel size $\Delta x$. For a uniform angular span of $\Delta \phi$ for the angular bins, this is achieved by selecting a uniform angular span ($\Delta \phi$) for the angular bins of at least about $\Delta \phi = \text{atan}(2g/\xi)$. This is derived for the TOF-LOR representing a symmetric Gaussian probability distribution that is independent of the angle of the LOR.

Figure 4:
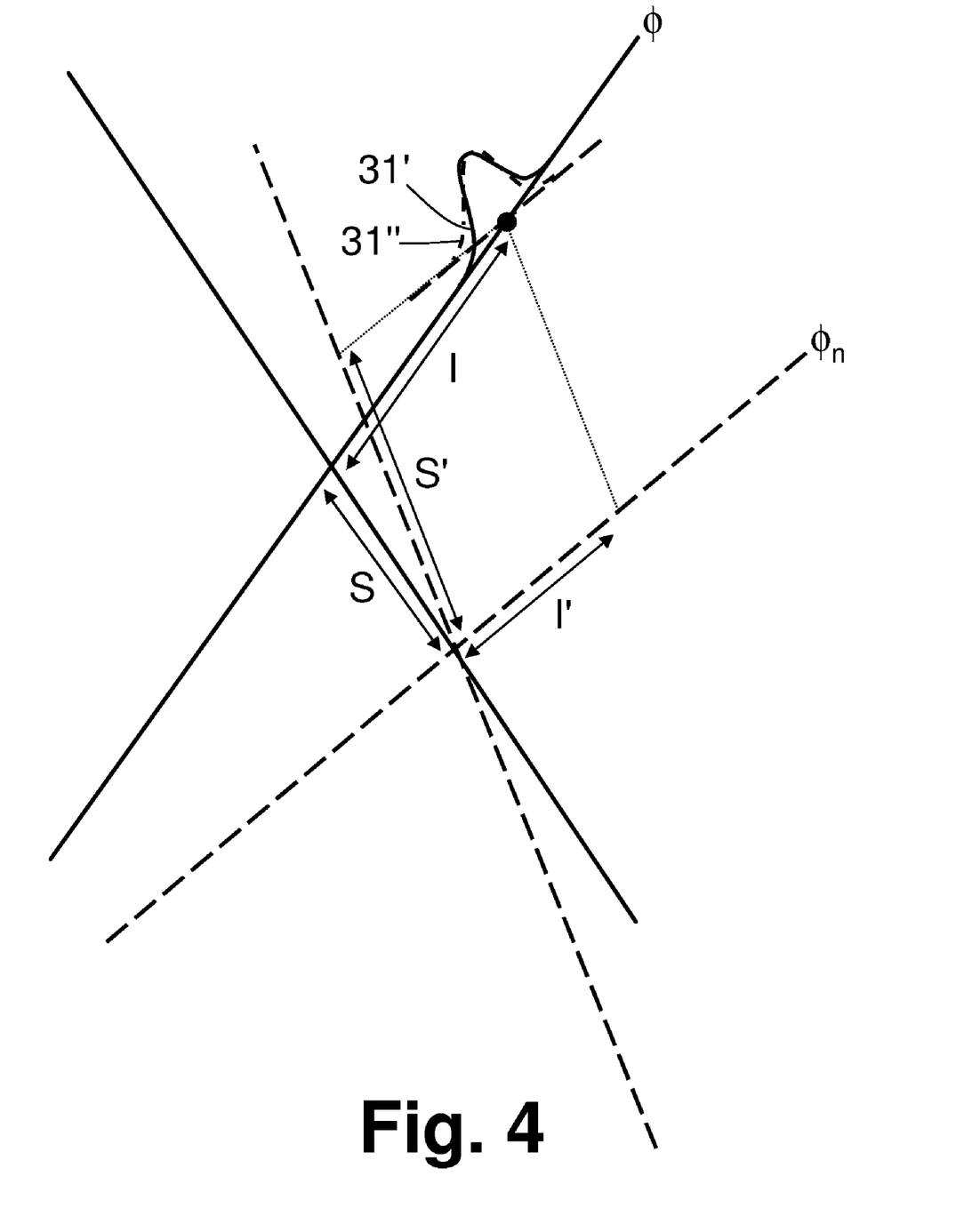
FIG. 4 diagrammatically shows one approach for coarse angular rebinning.

FIG. 4 illustrates one approach for coarse angular rebinning. The TOF-LOR 31' (after slice-binning) is illustrated in FIG. 4 showing the TOF information as a Gaussian profile drawn with a solid line. The TOF-LOR 31' is at an angle φ in the slice plane. An angularly rebinned TOF-LOR 31" is rebinned to an angular bin $\phi_n$, identified by index n. The TOF information for the angularly rebinned TOF-LOR 31" is shown as a Gaussian profile drawn with a broken line. The coordinate S shown in FIG. 4 is the radial distance between the line-of-response of the TOF-LOR 31' and the center of the scanner. The coordinate I identifies the position of the TOF- LOR 31' along the line-of-response. The coordinates S' and I' are the corresponding radial and TOF coordinates of the angularly rebinned TOF-LOR 31".

Figure 5:
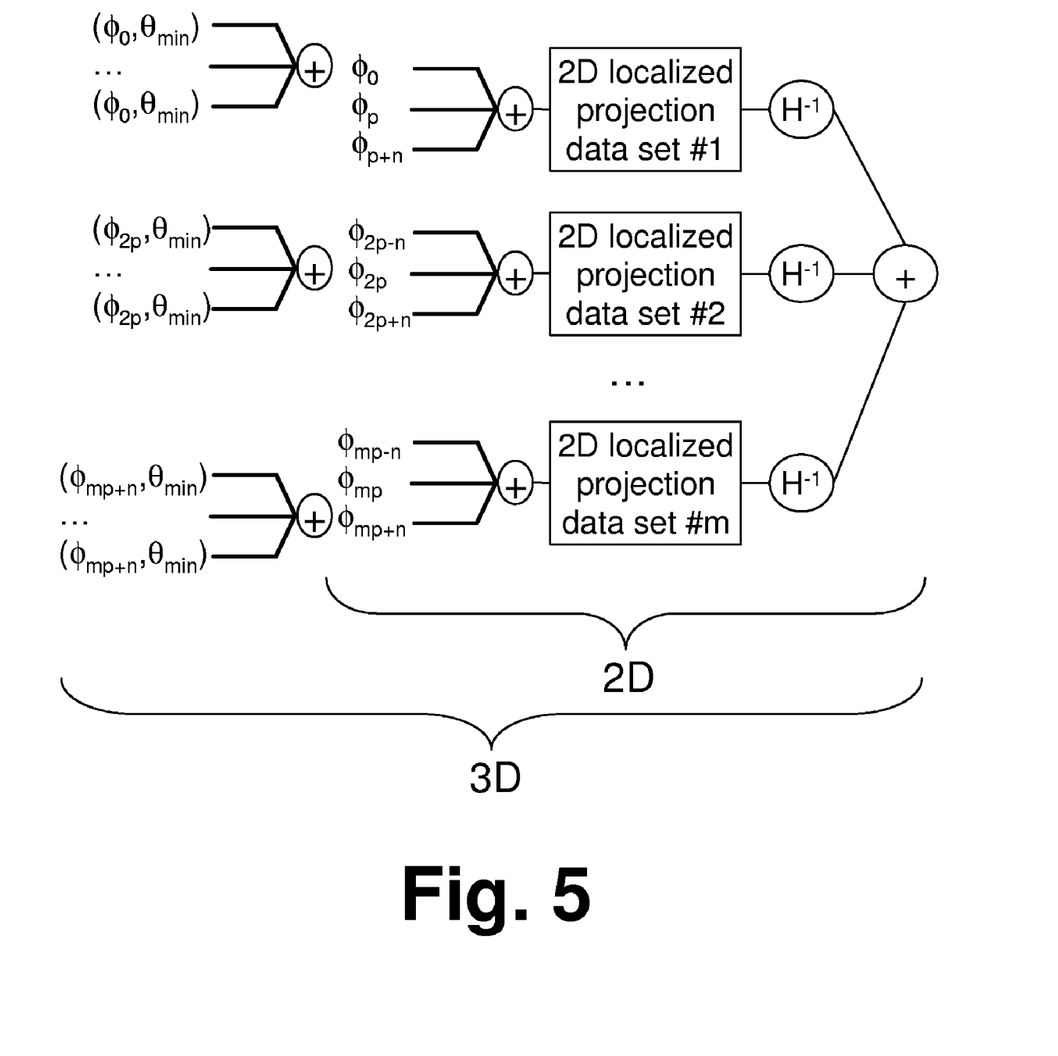
FIG. 5 diagrammatically shows a block diagram of an integrated three-dimensional TOF-PET reconstruction process suitably performed by the most likely slice rebinning processor and the two-dimensional reconstruction processor of the TOF-PET system of FIG. 1.

With reference to FIG. 5, the ordering of the TOF-LOR binning operations performed by the binning processors 40, 60 can be varied. FIG. 5 shows a block diagram of an integrated three-dimensional TOF-PET reconstruction process suitably performed by the most likely slice rebinning processor 40 and the two-dimensional reconstruction processor 50 is illustrated. TOF-LOR data with close orientations are added into different preimages for each angle. A preimage (or approximate image) is created for each angle and the most likely point of the positron-electron annihilation corresponding to each TOF-LOR, calculated using the time difference, for each "close" TOF-LOR is added to that preimage. Each preimage or approximate image is inverse time-of-flight filtered (shown as the $H^{-1}$ filters in FIG. 5) to produce the image slice.

With returning reference to FIG. 1, the skilled artisan will appreciate that the two-dimensional reconstruction processor 50 including the coarse angular rebinning can be applied directly to two-dimensional TOF-LOR data sets. For example, a TOF-PET scanner having a single ring of detectors directly acquires two-dimensional TOF-LOR data sets. Such a two-dimensional TOF-LOR data set can be directly input to the two-dimensional reconstruction processor 50, without the slice-binning since a PET scanner having a single detector ring acquires data only from a single slice, to provide a fast two-dimensional reconstruction taking advantage of the coarse angular rebinning.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. An imaging method comprising:
   acquiring three-dimensional positron emission tomography time-of-flight line-of-response (TOF-LOR) data, each TOF-LOR corresponding to a line-of-response with time-of-flight spatial localization;
   slice-binning the TOF-LOR data into a plurality of two-dimensional TOF-LOR data sets based on the time-of-flight spatial localization, at least some of the slice-binned TOF-LOR data corresponding to lines of response that are oblique to the two-dimensional data sets; and
   reconstructing the two-dimensional TOF-LOR data sets into corresponding image slices defining a three-dimensional reconstructed image, wherein the reconstructing of each two-dimensional TOF-LOR data set includes defining an approximate image as an aggregation of spatial points defined by the TOF-LORs of the two-dimensional TOF-LOR data set and inverse time-of-flight filtering the approximate image to produce the image slice.

2. The imaging method as set forth in claim 1, wherein the defining of the approximate image as the aggregation of spatial points defined by the TOF-LORs of the two-dimensional TOF-LOR data set includes:
   defining each spatial point as a most likely spatial position of a positron-electron annihilation event corresponding to the TOF-LOR.

3. The imaging method as set forth in claim 1, wherein the acquiring of TOF-LOR data employs a plurality of radiation detector rings each defining a spatial slice, and the slice-binning includes:
   for each oblique TOF-LOR, determining a most likely spatial position of a positron-electron annihilation event corresponding to that TOF-LOR; and
   binning each oblique TOF-LOR to a spatial slice containing the most likely spatial position of the positron-electron annihilation event corresponding to that oblique TOF-LOR.

4. A positron emission tomography (PET) scanner configured to perform the imaging method set forth in claim 1.

5. A processor programmed to perform the imaging method set forth in claim 1.

6. An imaging method comprising:
   acquiring three-dimensional positron emission tomography time-of-flight line-of-response (TOF-LOR) data, each TOF-LOR corresponding to a line-of-response with time-of-flight spatial localization;
   slice-binning the TOF-LOR data into a plurality of two-dimensional TOF-LOR data sets based on the time-of-flight spatial localization, at least some of the slice-binned TOF-LOR data corresponding to lines of response that are oblique to the two-dimensional data sets; and
   reconstructing the two-dimensional TOF-LOR data sets into corresponding image slices defining a three-dimensional reconstructed image, wherein the reconstructing of each two-dimensional TOF-LOR data set includes angularly binning the TOF-LOR data of the two-dimensional TOF-LOR data set to a plurality of angular bins and reconstructing the angularly binned TOF-LOR data to produce the image slice.

7. The imaging method as set forth in claim 6, wherein the angular binning includes:
   selecting a uniform angular span ($\Delta\phi$) for the angular bins of at least about $\Delta\phi=\mathrm{atan}(2g/\xi)$ where g equals a radius of a spatial region of interest divided by a statistical width of the TOF-LORs and $\xi$ equals a number of pixels spanning the spatial region of interest.

8. The imaging method as set forth in claim 6, wherein the number of angular bins is less than about twenty bins collectively spanning an angular span of 180°.

9. The imaging method as set forth in claim 6, wherein an angular span of each angular bin is at least about 10°.

10. The imaging method as set forth in claim 6, wherein the acquiring of TOF-LOR data employs a plurality of radiation detector rings each defining a spatial slice, and the slice-binning includes:
    for each oblique TOF-LOR, determining a most likely spatial position of a positron-electron annihilation event corresponding to that TOF-LOR; and
    binning each oblique TOF-LOR to a spatial slice containing the most likely spatial position of the positron-electron annihilation event corresponding to that oblique TOF-LOR.

11. A positron emission tomography (PET) scanner configured to perform the imaging method set forth in claim 6.

12. A processor programmed to perform the imaging method set forth in claim 6.

13. An imaging method comprising:
    acquiring positron emission tomography time-of-flight line-of-response (TOF-LOR) data, each TOF-LOR corresponding to a line-of-response with time-of-flight spatial localization;

coarsely angularly binning the TOF-LOR data to a plurality of coarse angular bins each having an angular span of at least about 10°; and reconstructing the coarsely angularly binned TOF-LOR data to produce the image slice.

14. A positron emission tomography (PET) scanner for performing the imaging method set forth in claim 13.

15. A processor programmed to perform the imaging method set forth in claim 13.

16. The imaging method as set forth in claim 13, wherein the coarse angular binning includes:

selecting a uniform angular span ($\Delta\phi$) for the angular bins of at least about $\Delta\phi = \text{atan}(2g/\xi)$ where g equals a radius of a spatial region of interest divided by a statistical width of the TOF-LORs, $\xi$ equals a number of pixels spanning the spatial region of interest, and $\Delta\phi$ is at least about 10°.

* * * * *